US00PP15944P3

(12) United States Plant Patent
Herman et al.

(10) Patent No.: US PP15,944 P3
(45) Date of Patent: Sep. 6, 2005

(54) BIRCH TREE NAME 'VERDALE'

(50) Latin Name: *Betula platyphylla*
Varietal Denomination: VerDale

(75) Inventors: Dale E. Herman, Fargo, ND (US); Larry J. Chaput, Fargo, ND (US); Zong-Ming Cheng, Knoxville, TN (US); Wenhao Dai, Fargo, ND (US); Victoria A. Magnusson, Hawley, MN (US)

(73) Assignee: NDSU Research Foundation, Fargo, ND (US)

( * ) Notice: Subject to any disclaimer, the term of this patent is extended or adjusted under 35 U.S.C. 154(b) by 98 days.

(21) Appl. No.: 10/768,784

(22) Filed: Jan. 30, 2004

(65) Prior Publication Data

US 2005/0172375 P1 Aug. 4, 2005

(51) Int. Cl.[7] ..... A01H 5/00
(52) U.S. Cl. ..... Plt./216
(58) Field of Search ..... Plt./216

*Primary Examiner*—Anne Marie Grunberg
(74) *Attorney, Agent, or Firm*—Jondle & Associates P.C.

(57) ABSTRACT

'VerDale' is a new cultivar of *Betula platyphylla,* Asian white birch. This new cultivar has white bark and dark green leaves in addition to being highly resistant to bronze birch borer (*Agrilus anxius* Gory).

2 Drawing Sheets

Genus and species: *Betula platyphylla.*
Cultivar denomination: 'VerDale'.

BACKGROUND OF THE INVENTION

The present invention comprises a new and distinct cultivar of birch tree, botanically known as *Betula platyphylla,* and hereinafter referred to by the cultivar name 'VerDale'. 'VerDale' is a product of a planned tree selection program which had the objective of creating a new cultivar of birch tree having high bronze birch borer resistance, good birch leafminer resistance and various aesthetic qualities as listed in the Detailed Description of the Plant.

The new cultivar is a selection of *Betula platyphylla,* and was discovered by applicant among seedlings grown from parental trees growing on the NDSU campus and was transplanted on Sep. 22, 1975 into the NDSU Research Arboretum, Absaraka, N. Dak. The selection was noticed by virtue of its long term bronze birch borer resistance; white bark; quality dark green foliage and excellent golden-yellow autumn foliage coloration; upright, oblong-elliptical form becoming broadly pyramidal with maturity.

The first act of asexual reproduction of 'VerDale' was accomplished when plants were produced in tissue culture using standard micropropagation techniques by applicant from the initial selection on Nov. 13, 2000 in a controlled environment in Fargo, N. Dak. (NDSU). Horticultural examination of selected units initiated on Nov. 13, 2000 has demonstrated that the combination of characteristics as herein disclosed for 'VerDale' are firmly fixed and are retained through successive generations of asexual reproduction.

'VerDale' has not been observed under all possible environmental conditions. The phenotype may vary with variations in environment such as temperature, light intensity, and day length. The following observations, measurements and comparisons describe the plants grown in the NDSU Research Arboretum or under greenhouse conditions, which approximate those generally used in commercial practices.

This new birch tree is illustrated by the accompanying photographs which show the entire tree, foliage closeup and bark features, the colors shown being as true as can be reasonably obtained by conventional photographic procedures.

DETAILED DESCRIPTION OF THE NEW PLANT

Figure 1:
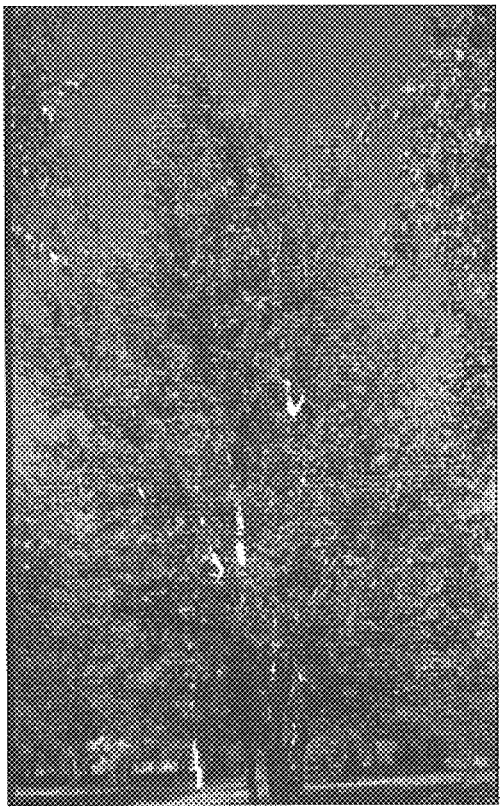
FIG. 1 shows the complete tree in dense foliage.
Figure 2:
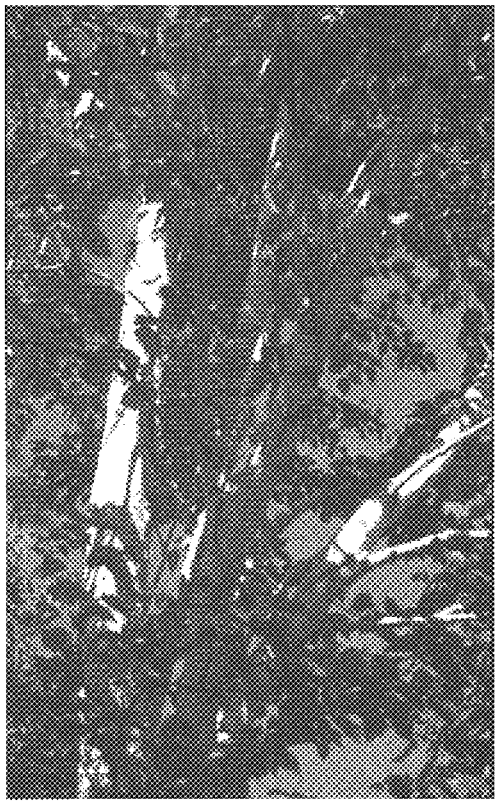
FIG. 2 shows the dense foliage.
Figure 3:
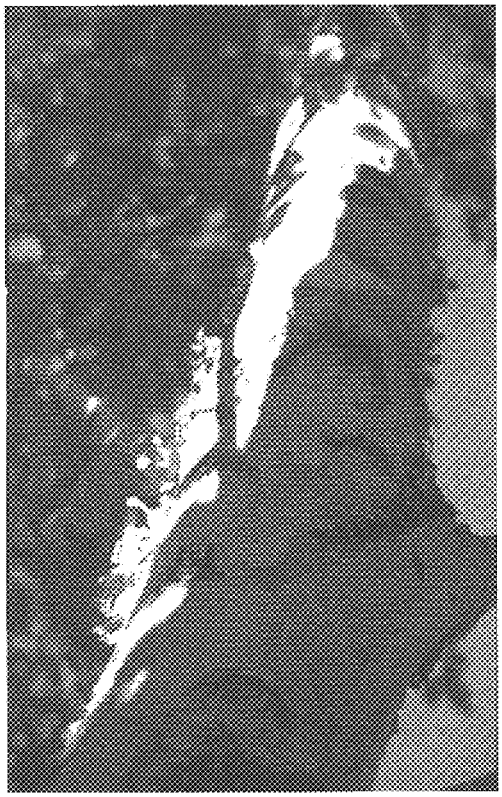
FIG. 3 shows the bark color and exfoliation on the trunks.
Figure 4:
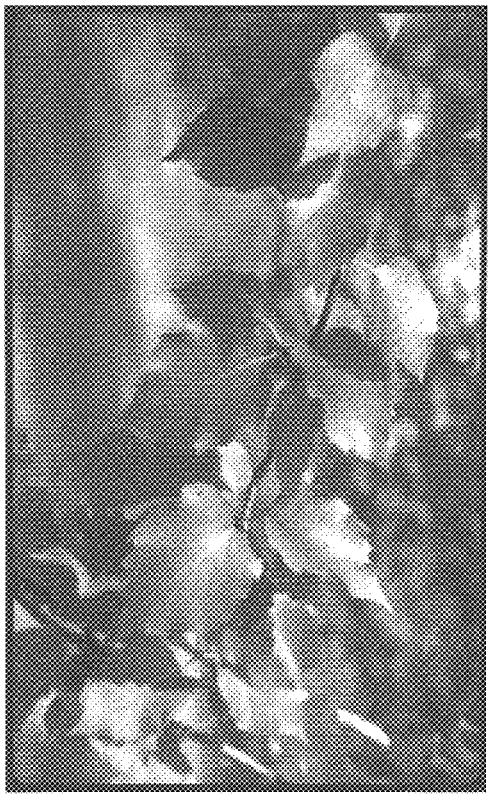
FIG. 4 is a close-up of the leaves.

The following traits and characteristics describe the new cultivar.

Classification:
*Origin.*—Seed source is unknown.
*Species.*—*Betula platyphylla.*
*Common names.*—Asian White Birch.

TREE

Trunk:
*Multiple stem.*—Two main trunks forming clump.
*Size.*—At 29 years of age, average diameter of two trunks, 30.7 cm measured at 127 cm above the ground.
*Bark.*—Color ranges from RHS 155B to RHS 155C, average length of exfoliating sheets 2.2 cm.
*Height.*—At 29 years of age, 14.6 m.
*Growth habit or form.*—Upright oblong to semi-pyramidal becoming broadly pyramidal with age.

*Growth rate.*—50.3 cm/year (under sod conditions in arboretum, no supplementary irrigation or fertilization).

Branches:

*Angle of attachment.*—Average angle of 25 branches, 47.0 degree.

*Spacing.*—Variable.

*Size.*—Crown diameter of tree, 6.3 m at 29 years.

*Bark.*—Prior to bark changing to white, branches aged 2–4 years range in color from greyed-orange (RHS 166A/B) to brown (RHS 200A).

Lenticels:

*Size.*—1–2 mm. on branches less than one inch in diameter.

*Color.*—Whitish.

*Quantity.*—Many.

Buds:

*Length.*—6–10 mm; average 8.2 mm.

*Width.*—2–3 mm; average 2.7 mm.

*Shape.*—Imbricate, pointed.

*Pubescence.*—Scattered.

*Bud pubescence color.*—RHS 200A (Brown).

*Bud color.*—Ranges from RHS 146B to RHS 146C.

*Time of leaf out.*—Varies from May 1–15.

Foliage:

*Size of leaf.*—Length — Range 7.5–10.7 cm, average 8.8 cm. Width — Range 5.2–7.9 cm, average 6.5 cm.

*Shape of leaf.*—Ovate-triangular to ovate-deltoid. Margin — Doubly-serrate. Texture — Medium.

*Pubescence distribution.*—Glabrous on both leaf surfaces, except scattered hairs on main vein (midrib) and lateral veins, more prevalent on bottom side.

*Color.*—Upper side, RHS 137A (green). Underside, RHS 148B (yellow-green).

*Autumn color.*—RHS 17C (yellow-orange).

*Petiole.*—Range from 1.9–2.8 cm, average 2.3 cm.

*Ribs and veins.*—Average of 9 vein pairs per leaf.

*Thorns and spines.*—None.

*Buds.*—Imbricate, pointed, scattered hairs.

CATKINS

Staminate:

*Shape.*—Cylindrical, dormant stage fairly rigid, blooming stage, pendulous.

*Size.*—Dormant stage length 1.2–2.8 cm, average 2.0 cm. Blooming stage 4.2–8.4 cm, average 6.4 cm.

Scales:

*Shape.*—Teardrop to diamond-shaped, dormant stage.

*Color.*—RHS 200D (brown) to RHS 6C/D (yellow).

Pistillate:

*Shape.*—Cylindrical; blooming stage, not pendulous.

*Size.*—Blooming stage 1.2–2.8 cm, average 2.0 cm.

Scales:

*Shape.*—Teardrop to diamond-shaped.

*Color.*—RHS 149A (yellow-green) to RHS 144C (yellow-green).

Timing of appearance, staminate, and pistillate catkins:

*Staminate.*—Develop during summer.

*Pistillate.*—Develop May 5–20.

*Timing of anthesis.*—May 1–15, varies with year.

Fruit: Strobile bearing, many winged nutlets (seeds) which average 5 mm long and 5 mm wide.

*Shape.*—Cylindrical.

*Length.*—2.7–4.2 cm, average 3.6 cm.

*Width.*—0.6–0.8 cm, average 0.7 cm.

*Color.*—Yellow-green (RHS 146C), changing to brown in the fall.

INSECT AND DISEASE RESISTANCE

No evidence of bronze birch borer attack in 29 years of evaluation in large birch collection in the NDSU Research Arboretum where borer population and death of other birch accessions has been high. Resistance to birch leaf miner has been good to date.

COMPARISON WITH MOST SIMILAR CULTIVAR

Of the many commercial birch trees known to the applicant, the most similar in comparison to 'VerDale' are the other introduced *Betula platyphylla* cultivars, such as *Betula platyphylla* 'Fargo' (U.S. Plant Pat. No. 10,963). The latter cultivar tends to have somewhat smaller and glossier leaves compared to 'Verdale' and it produces a narrow, columnar growth habit. The mature height of 'Fargo' is also less than 'VerDale'. In comparison to 'Fargo', 'VerDale' has a number of important attributes such as being highly bronze birch borer (*Agrilus anxius* Gory) resistant. The bark on stems of 'VerDale' begin changing to whitish at 8–15 mm in diameter. 'VerDale' has quality dark green foliage and excellent golden-yellow autumn foliage coloration. 'VerDale' has good resistance to birch leaf miner (*Fenusa pusilla* Lepeletier) and is very winterhardy (withstanding winter temperatures of −35° to −40° C.

What is claimed is:

1. A new and distinct *Betula platyphylla* birch tree as shown and described herein.

* * * * *